United States Patent
Patterson et al.

[11] Patent Number: 6,165,209
[45] Date of Patent: Dec. 26, 2000

[54] VASCULAR STENT FOR REDUCTION OF RESTENOSIS

[75] Inventors: Greg R. Patterson, Pleasanton; David J. Kupiecki, San Francisco; Kathy M. Mah, Mountain View; Ronald G. Williams, Menlo Park; James J. Leary, Sunnyvale, all of Calif.

[73] Assignee: Prolifix Medical, Inc., Sunnyvale, Calif.

[21] Appl. No.: 09/209,233

[22] Filed: Dec. 10, 1998

Related U.S. Application Data

[60] Provisional application No. 60/069,440, Dec. 15, 1997.

[51] Int. Cl.$^7$ ........................................................ A61F 2/06
[52] U.S. Cl. ................................................ 623/1.1; 606/159
[58] Field of Search ........................... 606/159, 198, 606/191; 623/1, 1.4, 1.15

[56] References Cited

U.S. PATENT DOCUMENTS

| | | |
|---|---|---|
| 4,345,414 | 8/1982 | Bornat et al. . |
| 5,059,166 | 10/1991 | Fischell et al. . |
| 5,078,736 | 1/1992 | Behl . |
| 5,151,105 | 9/1992 | Kwan-Gett . |
| 5,178,618 | 1/1993 | Kandarpa . |
| 5,298,018 | 3/1994 | Narciso, Jr. . |
| 5,383,892 | 1/1995 | Cardon et al. ........................ 606/198 |
| 5,419,760 | 5/1995 | Narciso, Jr. . |
| 5,422,362 | 6/1995 | Vincent et al. . |
| 5,441,497 | 8/1995 | Narciso, Jr. . |
| 5,454,794 | 10/1995 | Narciso et al. . |
| 5,545,569 | 8/1996 | Grainger et al. . |
| 5,549,663 | 8/1996 | Cottone, Jr. . |
| 5,571,169 | 11/1996 | Plaia et al. . |
| 5,613,946 | 3/1997 | McKeever . |
| 5,733,302 | 3/1998 | Myler et al. . |
| 5,766,192 | 6/1998 | Zacca ........................................ 606/159 |
| 5,769,884 | 6/1998 | Solovay . |
| 5,776,186 | 7/1998 | Uflacker . |
| 5,779,673 | 7/1998 | Roth et al. . |
| 5,843,162 | 12/1998 | Inoue . |

Primary Examiner—Gary Jackson
Assistant Examiner—Anthony S. King
Attorney, Agent, or Firm—Townsend and Townsend and Crew LLP

[57] ABSTRACT

Apparatus and methods are provided for restoring and maintaining an open passage or lumen in a body conduit, such as a blood vessel, which has become stenosed or occluded. The apparatus includes a stent which is specially adapted for inhibiting restenosis within the stent after implantation in a body passage. In various embodiments, the apparatus also includes a catheter or other device for operating the stent to inhibit restenosis within the stented region of the body passage. The methods presented include implanting the stent within a body passage, typically a blood vessel such as a coronary artery, which has become stenosed or occluded, and operating the stent to inhibit ingrowth of stenotic material which would result in restenosis of the stented region. The stent may be operated manually to inhibit or remove ingrowth of stenotic material, for example by introducing a catheter which acts on the stent, or the stent may operate automatically to inhibit or remove ingrowth of stenotic material without manual intervention.

4 Claims, 13 Drawing Sheets

VASCULAR STENT FOR REDUCTION OF RESTENOSIS

This application is a continuation of, and claims the benefit of priority from (provisional) application No. 60/069,440, filed on Dec. 15, 1997, the full disclosure of which is incorporated herein by reference.

BACKGROUND OF THE INVENTION

1. Field of the Invention

The present invention relates generally to apparatus and methods for restoring and maintaining an open passage in body conduits, such as blood vessels, which have become stenosed or occluded. More particularly, the present invention relates to a vascular stent for maintaining an open blood flow lumen in blood vessels and for preventing restenosis.

Percutaneous transluminal angioplasty (PTA) and percutaneous transluminal coronary angioplasty (PTCA) procedures are widely used for treating stenotic atherosclerotic regions of a patient's vasculature to restore adequate blood flow. Catheters having an expansible distal end, typically in the form of an inflatable balloon, are positioned in an artery, such as a coronary artery, at a stenotic site. The expansible end is then expanded to dilate the artery in order to restore adequate blood flow to regions beyond the stenosis. While PTA and PTCA have gained wide acceptance, these angioplasty procedures suffer from two major problems: abrupt closure and restenosis.

Abrupt closure refers to rapid reocclusion of the vessel within hours of the initial treatment, and often occurs in patients who have recently suffered acute myocardial infarction. Abrupt closure often results from either an intimal dissection or from rapid thrombus formation, which occurs, in response to injury of the vascular wall from the initial angioplasty procedure. Restenosis refers to a renarrowing of the artery over the weeks or months following an initially apparently successful angioplasty procedure. Restenosis occurs in up to 50% of all angioplasty patients and results at least in part from smooth muscle cell proliferation and migration.

Many different strategies have been proposed to ameliorate abrupt closure and reduce the rate of restenosis. Of particular interest to the present invention, the implantation of vascular stents following angioplasty has become widespread. Stents are thin-walled tubular scaffolds which are expanded in the arterial lumen following the angioplasty procedure. Most commonly, the stents are formed from a malleable material, such as stainless steel, and are expanded in situ using a balloon. Alternatively, the stents may be formed from a shape memory alloy or other elastic material, in which case they are allowed to self-expand at the angioplasty treatment site. In either case, the stent acts as a mechanical support for the artery wall, inhibiting abrupt closure and reducing the restenosis rate as compared to PTCA.

While stents have been very successful in inhibiting abrupt closure and reasonably successful in inhibiting restenosis, a significant portion of the treated patient population still experiences restenosis over time. Most stent structures comprise an open lattice, typically in a diamond or spiral pattern, and cell proliferation (also referred to as intimal hyperplasia) can intrude through the interstices between the support elements of the lattice. As a result, instead of forming a barrier to hyperplasia and restenosis, the stent can become embedded within an accumulated mass of thrombus and tissue growth, and the treatment site once again becomes occluded.

To date, proposed treatments for restenosis within previously stented regions of the coronary and other arteries have included both follow-up balloon angioplasty and directional atherectomy, e.g. using the Simpson directional atherectomy catheter available from Guidant Corporation, Santa Clara, Calif. Neither approach has been wholly successful. Balloon angioplasty can temporarily open the arterial lumen, but rarely provides long-term patency. Directional atherectomy can successfully debulk the lumen within the stent, but typically does not fully restore the stented lumen to its previous diameter because the catheter removes the stenotic material in an asymmetric pattern. Moreover, it has been found that the atherectomy cutting blades can damage the implanted stent. Such adverse effects were reported by Bowerman et al. in *Disruption of a coronary stent during atherectomy for restenosis* in the December 1991 issue of Catheterization and Cardiovascular Diagnosis and by Meyer et al. in *Stent wire cutting during coronary directional atherectomy* in the May 1993 issue of Clinical Cardiology. The possibility of such adverse outcomes is likely to limit the application of atherectomy as a treatment for stent restenosis and will probably result in more tentative use of the atherectomy cutter within the stented region when it is applied, leading to less complete removal of the stenosis.

For these reasons, it would be desirable to provide improved apparatus and methods for restoring and maintaining an open passage in blood vessels and other body conduits. More particularly, it would be desirable to provide a vascular stent for maintaining an open blood flow lumen in a blood vessel which inhibits restenosis within the stented region and which facilitates methods for treating restenosis within the stented region. The process of inhibiting or treating restenosis within the stent may be performed automatically by a mechanism within the stent or the process may be initiated by an extracorporeal activation means or, alternatively, the process may be performed by using catheter-based, minimally invasive techniques for removing stenotic material from within the stented region.

2. Description of the Background Art

Although a great deal of attention and effort has been focused on the problem of in-stent restenosis very few workable solutions have actually been proposed. One proposed solution is the use of intravascular radiation therapy at the stented site to inhibit smooth muscle cell proliferation and to reduce the incidence of in-stent restenosis. Examples of this approach include U.S. Pat. Nos. 5,059,166, and 5,545,569. Systems for applying intravascular radiation treatment can be divided into two general categories: a) catheter or guidewire based treatment systems for delivering a radioisotope to the treatment site for short term irradiation of the stented region; and b) radioactive stents implanted at the treatment site for longer term irradiation of the stented region. Radioisotopes used in both of these approaches typically include gamma emitters, such as Iridium 192, which have the properties of high tissue penetration and a long radioactive half-life, and beta emitters, such as Phosphorus 32 and Strontium 90, which have the properties of low tissue penetration and a shorter radioactive half-life. Although initial testing of intravascular radiation therapy for reduction of in-stent restenosis has been promising, no one knows what the long-term benefits or the adverse effects of the radiation treatment will be. However, even in the most optimistic scenarios, intravascular radiation treatment is not expected to completely eliminate in-stent restenosis. This uncertainty, coupled with the inconvenience and the potential hazards to health care workers of handling radioactive isotopes, points out the importance of finding other alternatives to this experimental approach.

Another proposed solution is described in U.S. Pat. No. 5,078,736 wherein energy, such as mechanical, heat or radio frequency energy, is periodically applied to a stent implanted in a hollow body duct to inhibit the growth of tissue through the interstices of the stent. The patent describes the use of this method in the ureter, the biliary ducts, respiratory passages, pancreatic ducts, lymphatic ducts, and the like. It is uncertain what the effect of this approach would be in the vascular system where applying energy sufficient to inhibit cell growth may be enough to also trigger undesirable events, such as coagulation of the blood in the vicinity of the stent.

Yet another approach involves the application of light energy, either in the infrared, visible or ultraviolet region, to irradiate the stent and the surrounding area to inhibit the growth of tissue through the interstices of the stent. This approach, sometimes referred to as photodynamic therapy, may be used independently or as an adjunct to angioplasty and stenting. Examples of this approach are described in U.S. Pat. Nos. 5,454,794, 5,441,497, 5,422,362, 5,419,760, and 5,298,018. Although research is ongoing, photodynamic therapy has not yet proven itself to be effective for prevention of in-stent restenosis.

The disclosures of each of the patents referenced above are incorporated herein by reference in their entirety. Each of the approaches represented by these patents has potential drawbacks and none of these experimental approaches has yet been proven to be completely effective for prevention of in-stent restenosis. Consequently, it remains highly desirable to identify and develop a successful treatment for atherosclerosis that will prevent the problem of in-stent restenosis.

SUMMARY OF THE INVENTION

The present invention provides apparatus and methods for restoring and maintaining an open passage or lumen in a body conduit, such as a blood vessel or other body passage, which has become stenosed or occluded. The present invention is particularly intended for inhibiting restenosis within a treated blood vessel which could result from ingrowth or accumulation of cellular, thrombotic, and other material within the lumen of the blood vessel. The apparatus of the present invention includes a stent which is specially adapted for inhibiting restenosis within the stent after implantation in a body passage. In a preferred embodiment, the stent includes a frame with passages through the frame and a component which is movable relative to the frame to remove stenotic material intruding through the passages. In various embodiments of the invention, the apparatus also includes a catheter or other device for operating the stent to inhibit restenosis within the stented region of the body passage.

Methods according to the present invention comprise implanting the stent within a body passage, typically a blood vessel such as a coronary artery or other artery, which has become stenosed or occluded, and operating the stent to inhibit ingrowth of stenotic material which would result in restenosis of the stented region. In a preferred method, a component on the stent is moved relative to the frame of the stent to remove stenotic material intruding through the passages of the stent. The stent may be operated manually to inhibit or remove ingrowth of stenotic material, for example by introducing a catheter which acts on the stent, or the stent may operate automatically to inhibit or remove ingrowth of stenotic material without manual intervention.

In a first illustrative embodiment of the invention, the apparatus includes a stent in the shape of a hollow, open-ended cylinder having an outer layer and an inner layer. The stent is deployable from a small diameter, compressed state to a larger diameter, expanded state. The outer layer comprises a frame incorporating a matrix of support members separated by openings or interstices. The inner layer also comprises a matrix of support members separated by openings or interstices. The support members of the inner and outer layers may be formed of wire or may be formed by slotting or cutting a tubular member to create a desired pattern of support members and interstices. The pattern of the inner and outer layers may be the same or different. The inner layer is movable within the outer layer, by translation and/or rotation. When the inner layer is moved within the outer layer, the support members of the inner layer move past the openings of the outer layer, and vice versa, creating a sort of wiper action which removes stenotic material intruding through the openings of the inner and outer layers. If this wiper action is performed at regular intervals ingrowth of stenotic material will be held to a minimum and any particles created by the cleaning action of the stent will be small enough as to not present any significant danger of embolization. To provide a flexible stent, the inner layer and/or the outer layer of the stent can be made in short segments joined together end-to-end by flexible connectors. The apparatus of the present invention will also comprise a means for moving the inner layer with respect to the outer layer, which may take one of several forms.

In one variation of the first embodiment the means for moving the inner layer with respect to the outer layer comprises a catheter for engaging the inner and the outer layers and moving them with respect to one another by translation and/or rotation. In other variations of the first embodiment the means for moving the inner layer with respect to the outer layer comprises one or more actuation members incorporated into the stent. The actuation members may be activated by temperature, pressure or flow to move the inner and the outer layers with respect to one another by translation and/or rotation.

In a second illustrative embodiment of the invention, the apparatus includes a stent in the shape of a hollow, open-ended cylinder having a self-cleaning mechanism incorporated into the wall of the stent. The stent is deployable from a small diameter, compressed state to a larger diameter, expanded state. The self-cleaning mechanism of the stent generally includes one or more wiper members, which in some embodiments may also serve as support members of the stent. When activated, the wiper members move over the openings between the support members of the stent to inhibit or remove ingrowth of stenotic material within the stent. The wiper members may be activated to move by sonic or ultrasonic energy, electrical energy, temperature or pressure.

In a third illustrative embodiment of the invention, the apparatus includes a stent in the shape of a hollow, open-ended cylinder having an outer layer and a removable inner layer. The stent is deployable from a small diameter, compressed state to a larger diameter, expanded state. The outer layer comprises a matrix of support members separated by openings or interstices. The removable inner layer is coextensive with the outer layer and is preferably made of a microporous or impermeable material which will serve as an effective barrier to ingrowth of stenotic material. Additionally or alternatively, the inner layer may contain an antimitotic agent to stop smooth cell proliferation. The apparatus also comprises a retrieval catheter device for removing and retrieving the removable inner layer after implantation of the stent.

In a fourth illustrative embodiment of the invention, the apparatus includes a stent which is specially adapted for facilitating removal of stenotic material from within the stent and a catheter which is adapted for use with the stent. The stent is deployable from a small diameter, compressed state to a larger diameter, expanded state. The stent has multiple internal rails, which may be a slots or grooves within the wall of the stent. The catheter is made with a like number of extendable and retractable legs that end in feet, which are specially shaped to ride in the slots or grooves of the rails. The feet guide the catheter longitudinally along the rails on the interior of the stent and center the catheter within the stent. The catheter includes a stenotic material removal mechanism, which may be a cutter, a brush, an abrasion tool, an ablation device, a vacuum aspiration device or any other means for removing stenotic material from within the stent. The internal rails of the stent guide the stenotic material removal mechanism and keep it centered within the stent for effective removal of stenotic material without damage to the stent or to the native vessel walls surrounding the stent.

Each illustrative embodiment of the invention may be presented as a sterile kit containing a stent and a stent delivery catheter, mounted on a board or in a tray, instructions for use (IFU), and a pouch or other conventional package. A retrieval catheter or a stenotic material removal catheter may be packaged together with the catheter kit or separately.

DESCRIPTION OF THE PREFERRED EMBODIMENT

Figure 1:
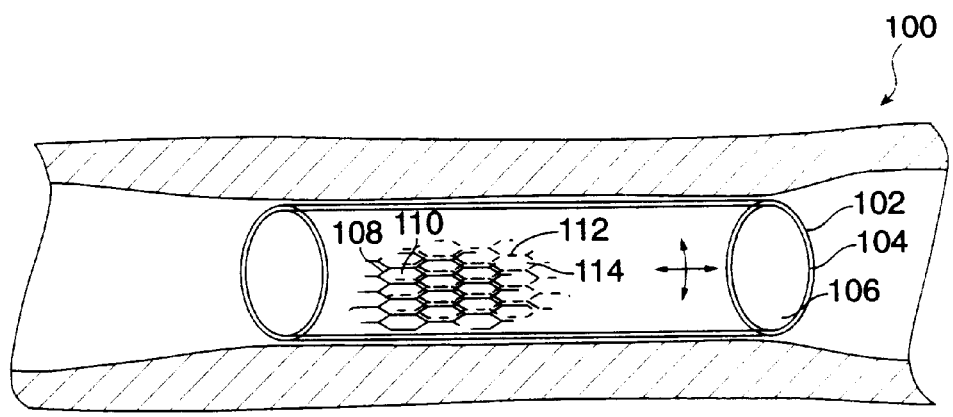
FIG. 1 shows a first embodiment of the stent apparatus of the present invention having an outer layer and a movable inner layer in the expanded or deployed state.
Figure 2:
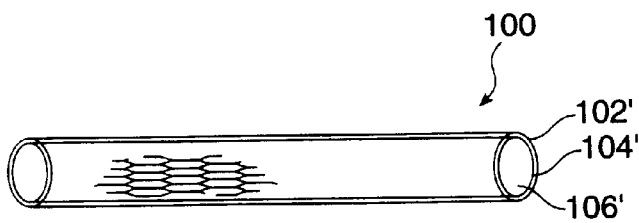
FIG. 2 shows the stent apparatus of FIG. 1 in the compressed state.

FIGS. 1 and 2 show a first embodiment of the apparatus of the present invention. The apparatus comprises a stent 100 having an outer layer 102 and an inner layer 104. Preferably, the stent 100 is configured to have the general shape of a hollow, open-ended cylinder with an internal lumen 106. The stent 100 is deployable from a compressed state to an expanded state. When the stent 100 is in the compressed state, as shown in FIG. 2, it has a reduced diameter to facilitate percutaneous and transluminal delivery of the stent 100 to the stenting site. In the expanded or deployed state, the stent 100 has an enlarged diameter which serves to support the walls of the body vessel into which the stent 100 is implanted in order to keep the vessel lumen open, as shown in FIG. 1. For use in coronary arteries, the stent 100 preferably has an expanded diameter from approximately 2 mm to 5 mm. For use in peripheral arteries, the stent 100 may have an expanded diameter from approximately 4 mm to 10 mm. For use in other body passages, the stent 100 should be adapted to have an expanded diameter approximately matching the desired luminal diameter of the body passage. The length of the stent 100 is highly variable. For use in coronary arteries, the stent 100 preferably has a length from approximately 10 mm to 60 mm. For use in peripheral arteries and other body passages, the stent 100 may be made considerably longer, if required. The stent 100 may be deployed by mechanical expansion means, such as by expanding an angioplasty balloon or other mechanical device within the lumen 106 of the stent 100. Alternatively, the stent 100 may be self-deploying, for example by elastic expansion or shape-memory expansion of the stent 100.

In the deployed state, the outer layer 102 of the stent 100 defines a first cylinder of a first diameter constituted by a frame incorporating a matrix of support members 108 separated by openings or interstices 110. The support members 108 may be formed of wire or may be formed by slotting or cutting a tubular member to create a desired pattern of support members 108 and interstices 110. The inner layer 104 defines a second cylinder with a slightly smaller diameter and concentric with the first cylinder of the outer layer 102, which is also constituted by a matrix of support members 112 separated by openings or interstices 114. The support members 112 of the inner layer 104 may also be formed of wire or may be formed by slotting or cutting a tubular member to create a desired pattern of support members 112 and interstices 114. The pattern of the inner layer 104 may be the same or different from the pattern of the outer layer 102. For example, it may be desirable under some circumstances to make the outer layer 102 of the stent 100 with a fine mesh of support members 108 and interstices 110 to provide optimum support for the arterial walls, while the inner layer 104 may have a coarser pattern with fewer support members 112 and larger interstices 114, or vice versa.

The inner layer 104 is movable with respect to the outer layer 102, by translating and/or rotating the inner layer 104 within the outer layer 102. When the inner layer 104 is moved within the outer layer 102, the support members 112 of the inner layer 104 move past the openings 110 of the outer layer 102, and vice versa, creating a sort of wiper action which removes stenotic material intruding through the openings of the inner and outer layers. If this wiper action is performed at regular intervals ingrowth of stenotic material will be held to a minimum and any particles created by the cleaning action of the stent 100 will be small enough as to not present any significant danger of embolization. To provide a flexible stent, the inner layer 104 and/or the outer layer 102 of the stent 100 can be made in short segments joined together end-to-end by flexible connectors. In a preferred embodiment, the apparatus of the present invention will also comprise a means for moving the inner layer 104 with respect to the outer layer 102, which may take one of several forms.

Figure 3:
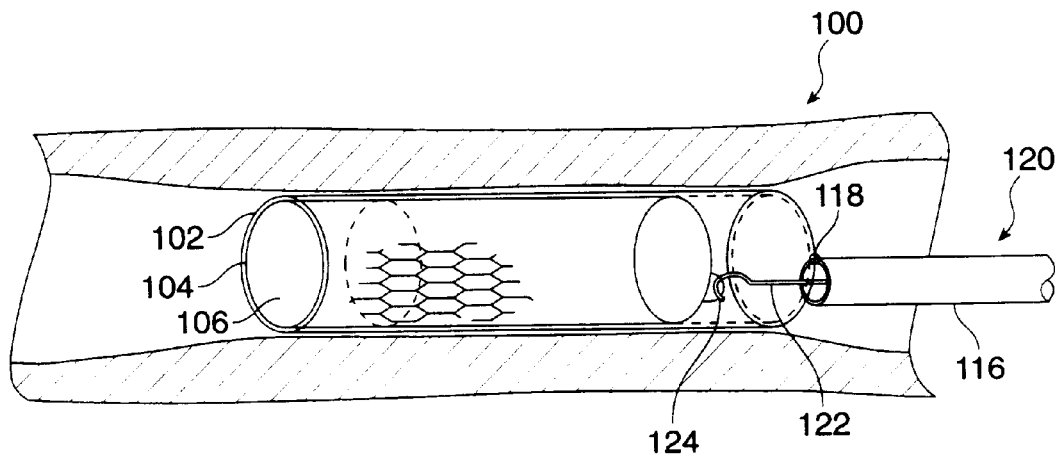
FIG. 3 shows a variation the stent apparatus of FIG. 1 with a catheter for actuating the stent.

FIG. 3 shows an embodiment of the apparatus of FIGS. 1 and 2 in which the stent 100 comprises an outer layer 102 and an inner layer 104, as described above, and the means for moving the inner layer 104 with respect to the outer layer 102 comprises a catheter 120. The catheter 120 includes a first elongated member 116, having means 118 for engaging the outer layer 102, and a second elongated member 122, having means 124 for engaging the inner layer 104. The second elongated member 122 is movable with respect to the first elongated member 116 by translation and/or rotation. Thus, the inner layer 104 is movable with respect to the outer layer 102 by engaging the stent 100 with the catheter 120 and moving the second elongated member 122 with respect to the first elongated member 116.

The catheter 120 and each of its components may take many possible forms. By way of example, the catheter 120 of FIG. 3 is configured with an outer tube that serves as the first elongated member 116. The outer tube 116 has a hook, snare, grasper or other means 118 for engaging the outer layer 102 of the stent 100. Within the outer tube 116 is a movable inner wire, cable or tube that serves as the second elongated member 122. The inner wire 122 has a hook, snare, grasper or other means 124 for engaging the inner layer 104 of the stent 100. When it is necessary to clear an implanted stent 100 of stenotic ingrowth, the catheter 120 is introduced percutaneously and advanced intraluminally to the site of the stent 100. The outer tube 116 of the catheter 120 grasps or engages the outer layer 102 of the stent 100 and the inner wire 122 engages the inner layer 104 of the stent 100. Then, the inner wire 122 is moved within the outer tube 116 by translation and/or rotation to translate and/or rotate the inner layer 104 of the stent 100 with respect to the outer layer 102, in the process, removing any ingrowth of stenotic material intruding through the openings of the stent 100.

If the stent 100 is intended for actuation by axially or longitudinally translating the inner layer 104 of the stent 100 with respect to the outer layer 102, then, preferably, the inner layer 104 is made slightly shorter in length than the outer layer 102 so that the inner layer 104 can move axially within the confines of the outer layer 102 so that the surrounding unstented native arterial walls are not disturbed or abraded by the cleaning action of the stent 100. If the pattern of support members 108 and interstices 110 within the stent 100 has repeating units, then the difference in length between the inner layer 104 and the outer layer 102 will, by preference, be equivalent to the length of at least one repeating unit in order to assure an effective wiping action between the inner layer 104 and the outer layer 102 of the stent 100. This attribute is shown somewhat exaggerated in FIG. 3 for the purposes of illustration.

Figure 4:
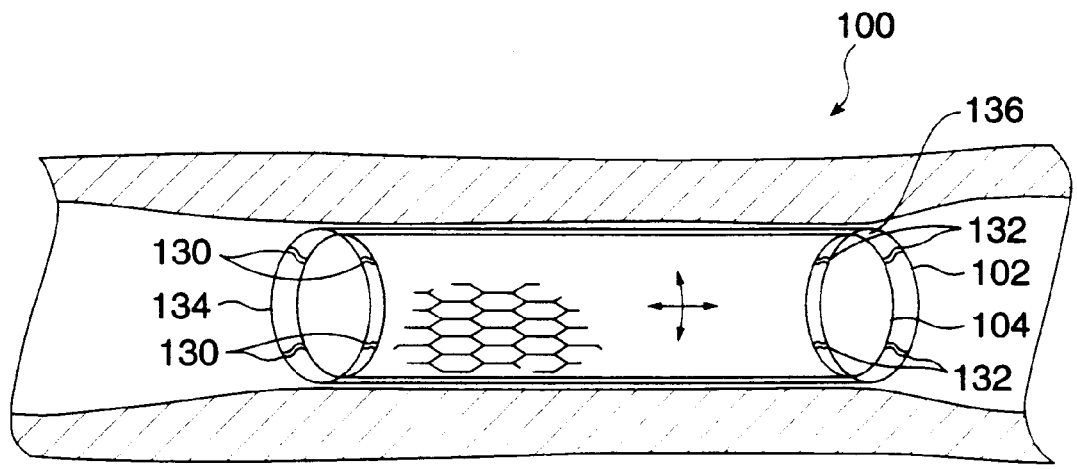
FIG. 4 shows a variation of the stent apparatus of FIG. 1 with thermally activated shape memory material actuation members.

FIG. 4 shows an embodiment of the apparatus of FIGS. 1 and 2 in which the stent 100 comprises an outer layer 102 and an inner layer 104, and the means for moving the inner layer 104 with respect to the outer layer 102 comprises at least one actuation member 130, 132. In this illustrative example, the stent 100 is shown as having eight actuation members 130, 132 linking the ends of the inner layer 104 with the respective ends of the outer layer 102 of the stent 100. The actuation members 130, 132 are configured to be controllable or actuatable to move the inner layer 104 with respect to the outer layer 102 in response to an imposed stimulus.

In one preferred embodiment of the apparatus, the actuation members 130, 132 are made of a thermally activated shape memory material, such as a nickel/titanium shape memory alloy or a thermally activated bimetallic strip, which changes its shape and/or dimensions in response to a change in temperature. The thermally activated shape memory material of the actuation members 130, 132 may be chosen to have an activation temperature that is outside of the range of normal body temperatures, so that a temperature change must be externally imposed upon the stent in situ. Such a temperature change may be externally imposed by flushing the artery or other body passage with cooled or heated saline solution or blood to activate the actuation members 130, 132 to move the inner layer 104 within the outer layer 102, thereby removing any ingrowth of stenotic material intruding through the openings of the stent 100. Alternatively, the actuation members 130, 132 of the stent 100 may be heated percutaneously by the application of electromagnetic energy to activate the cleaning action of the stent 100, for example by applying radiofrequency or microwave energy. As another alternative, the thermally activated shape memory material of the actuation members 130, 132 may be chosen to have an activation temperature within the normal range of diurnal body temperature fluctuations. Thus, the actuation members 130, 132 will be activated to perform the cleaning action of the stent 100 on a daily basis.

The actuation members 130, 132 may be configured to move the inner layer 104 within the outer layer 102 by translation and/or by rotation. For example, the stent 100 may be configured so that the actuation members 130 on a first end 134 of the stent 100 expand in response to a rise in temperature and contract in response to a drop in temperature, while 132 the actuation members 132 on a second end 136 of the stent 100 contract in response to a rise in temperature and expand in response to a drop in temperature. Thus, when the stent 100 is heated, the inner layer 104 will be urged to move in a direction from the first end 134 toward the second end 136 of the stent 100, and when the stent 100 is cooled, the inner layer 104 will be urged to move in the opposite direction from the second end 136 toward the first end 134 of the stent 100. Ingrowth of stenotic material intruding through the openings of the stent 100 can be kept to a minimum by periodically cycling the temperature of the implanted stent 100 to induce a self-cleaning action.

Figure 5:
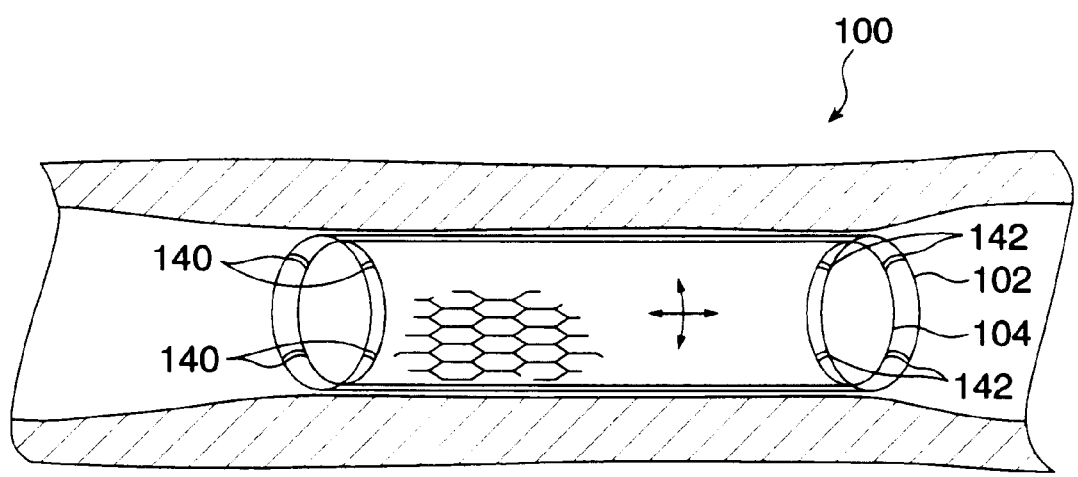
FIG. 5 shows a variation of the stent apparatus of FIG. 1 with pressure activated actuation members.

FIG. 5 shows an embodiment of the apparatus of FIGS. 1 and 2 in which the stent 100 comprises an outer layer 102 and an inner layer 104, and the means for moving the inner layer 104 with respect to the outer layer 102 comprises at least one pressure activated actuation member 140, 142. In this illustrative example, the stent 100 is shown as having eight pressure activated actuation members 140, 142 linking the ends of the inner layer 104 with the respective ends of the outer layer 102 of the stent 100. The actuation members 140, 142 are configured to change their shape and/or dimensions in response to a change in the environmental pressure surrounding the stent 100 and thus to move the inner layer 104 of the stent 100 with respect to the outer layer 102.

The pressure activated actuation members 140, 142 may be made in a number of different configurations. For example, the actuation members 140, 142 may be made in the configuration of miniature sealed Bourdon tubes linking the inner layer 104 to the outer layer 102 of the stent 100, as shown in FIG. 5. The Bourdon tubes 140, 142 have a curvature which tends to increase or decrease in proportion to the differential pressure between the outside of the tube and the inside of the tube. Other possible configurations for the pressure activated actuation members 140, 142 include sealed bellows, which expand and contract in response to changes in environmental pressure, or miniature cylinders with pistons which move in response to changes in environmental pressure. The pressure activated actuation members 140, 142 may be configured to move the inner layer 104 within the outer layer 102 by translation and/or by rotation. Thus, the inner layer 104 can be induced to move with respect to the outer layer 102 by cycling the environmental pressure exterior to the pressure activated actuation members 140, 142, thereby removing any ingrowth of stenotic material intruding through the openings of the stent 100. This can be accomplished by placing the patient in a hyperbaric and/or hypobaric chamber and cycling the pressure within safe limits. Alternatively, the pressure activated actuation members 140, 142 can be configured to be actuated by normal fluctuations in blood pressure or atmospheric pressure.

Figure 6:
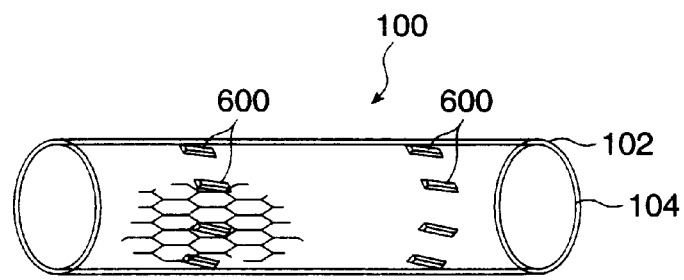
FIG. 6 shows a variation of the stent apparatus of FIG. 1 with a flow activated actuation member.

FIG. 6 shows an embodiment of the apparatus of FIGS. 1 and 2 in which the stent 100 comprises an outer layer 102 and an inner layer 104, and the means for moving the inner layer 104 with respect to the outer layer 102 comprises a flow activated actuation member 600. In this illustrative example, the flow activated actuation member 600 is shown as plurality of turbine blades on the inner layer 104 of the stent 100. Fluid flow, e.g. blood flow, through the lumen 106 of the stent 100 urges the inner layer 104 to rotate with respect to the outer layer 102, thereby removing any ingrowth of stenotic material intruding through the openings of the stent 100. The rotation of the inner layer 104 can be continuous, intermittent or reciprocal, as desired. Alternatively, the flow activated actuation member 600 can be configured to cause the inner layer 104 to reciprocate axially or to reciprocate axially and rotate with respect to the outer layer 102.

Figure 7:
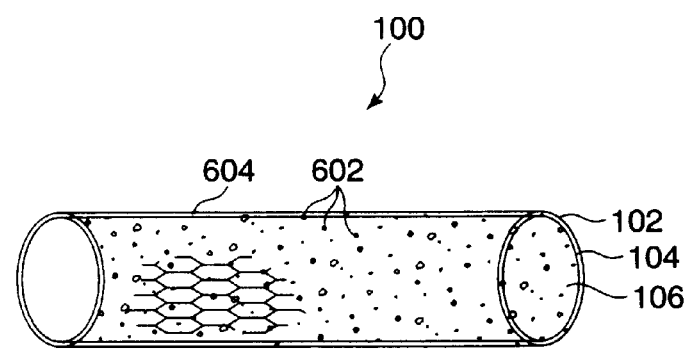
FIG. 7 shows a variation of the stent apparatus of FIG. 1 with flow activated actuation members.

FIG. 7 shows an embodiment of the apparatus of FIGS. 1 and 2 in which the stent 100 comprises an outer layer 102 and an inner layer 104. The inner layer 104 is freely movable with respect to the outer layer 102 so that it can move in response to fluid flow, e.g. blood flow, through the lumen 106 of the stent 100. Alternatively, the inner layer 104 may be bonded at both ends to the outer layer 102, but be flexible enough so that it can move in response to fluid flow. A multiplicity of particles 602 are located in the annular space 604 between the inner layer 104 and the outer layer 102. The particles 602 may be bonded to the inner layer 104 or they may be freely moving within the annular space 604. The particles 602 may be smoothly rounded or they may be rough abrasive particles. Fluid flow through the lumen 106 of the stent 100 urges the inner layer 104 and/or the particles 602 to move with respect to the outer layer 102. Abrasion between the particles 602 and the outer layer 102 removes any ingrowth of stenotic material intruding through the openings of the stent 100.

Figure 8:
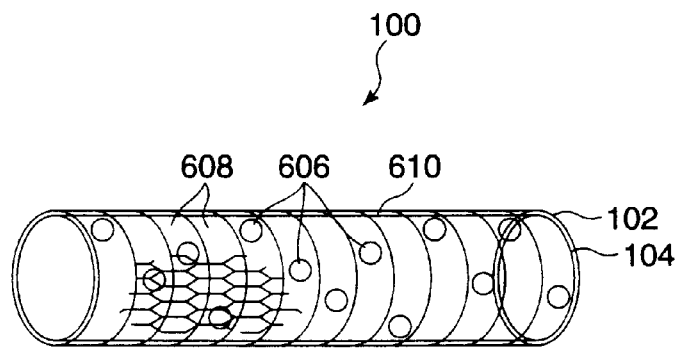
FIG. 8 shows another variation of the stent apparatus of FIG. 1 with flow activated actuation members.

FIG. 8 shows a variation of the embodiment of FIG. 7 in which the moving particles are spherical particles 606 that are constrained to move within predetermined pathways 608 formed in the annular space 610 between the inner layer 104 and the outer layer 102 of the stent 100. The pathways 608 in the annular space 610 between the inner layer 104 and the outer layer 102 may be formed circumferentially, longitudinally, diagonally or in a complex pattern, e.g. in a serpentine path, with respect to the stent 100.

Figure 9:
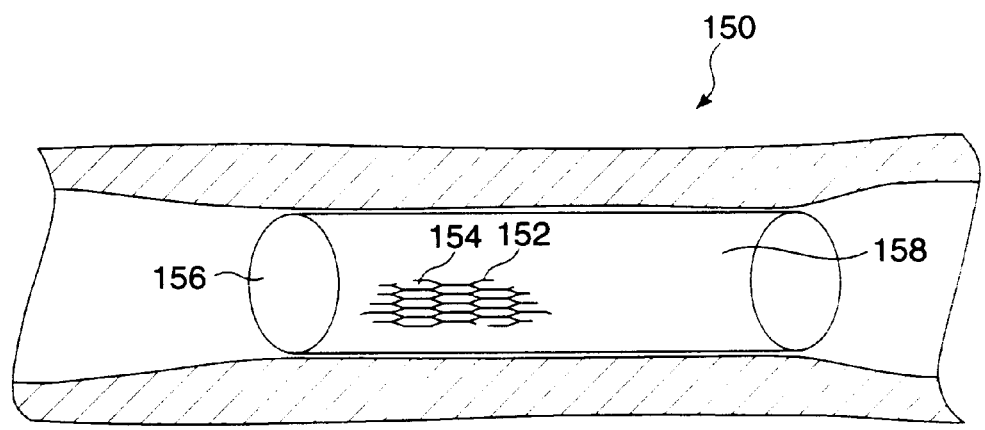
FIG. 9 shows a second embodiment of the stent apparatus of the present invention incorporating a self-cleaning mechanism in the expanded or deployed state.
Figure 10:
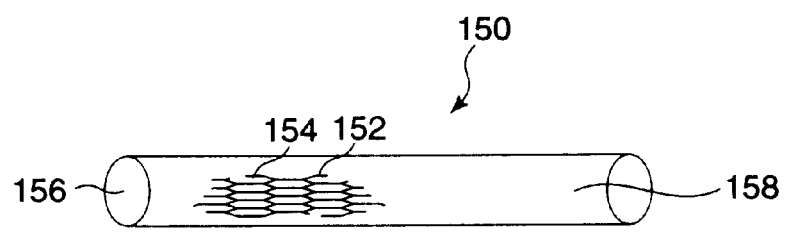
FIG. 10 shows the stent apparatus of FIG. 9 in the compressed state.

FIGS. 9 and 10 show a second embodiment of the apparatus of the present invention. The apparatus comprises a stent 150 having a self-cleaning mechanism incorporated into the wall 158 of the stent 150. The stent 150 is configured to have the general shape of a hollow, open-ended cylinder with an internal lumen 156. The stent 150 is deployable from a compressed state to an expanded state. When the stent 150 is in the compressed state, as shown in FIG. 10, it has a reduced diameter to facilitate percutaneous and transluminal delivery of the stent 150 to the stenting site. In the expanded or deployed state, the stent 150 has an enlarged diameter which serves to support the walls of the body vessel into which the stent 150 is implanted in order to keep the vessel lumen open, as shown in FIG. 9. For use in coronary arteries, the stent 150 preferably has an expanded diameter from approximately 2 mm to 5 mm. For use in peripheral arteries, the stent 150 may have an expanded diameter from approximately 4 mm to 10 mm. For use in other body passages, the stent 150 should be adapted to have an expanded diameter approximately matching the desired luminal diameter of the body passage. The length of the stent 150 is highly variable. For use in coronary arteries, the stent 150 preferably has a length from approximately 15 mm to 60 mm. For use in peripheral arteries and other body passages, the stent 150 may be made considerably longer, if required. The stent 150 may be deployed by mechanical expansion means, such as by expanding an angioplasty balloon or other mechanical device within the lumen 156 of the stent 150. Alternatively, the stent 150 may be self-deploying, for example by elastic expansion or shape-memory expansion of the stent 150.

Preferably, the wall 158 of the stent 150 is constructed with at least one layer constituted by a matrix of support members 152 separated by openings or interstices 154. The support members 152 of the stent 150 may be formed of wire or may be formed by slotting or cutting a tubular member to create a desired pattern of support members 152 and interstices 154. The self-cleaning mechanism is incorporated into the wall 158 of the stent 150 by configuring the support members 152 to be controllable or actuatable to move and/or change shape in response to an external stimulus. The motion of the support members 152 creates a sort of wiper action across the openings 154 in the wall 158 of the stent 150, which removes stenotic material intruding through the openings 154. If this wiper action is performed at regular intervals ingrowth of stenotic material will be held to a minimum and any particles created by the cleaning action of the stent 150 will be small enough as to not present any significant danger of embolization.

Figure 11:
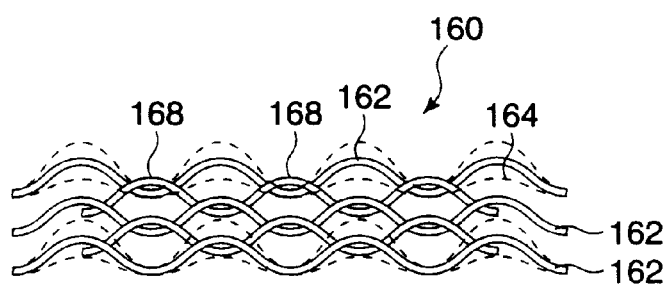
FIG. 11 is a magnified view of a first variation of the stent apparatus of FIG. 9.

FIG. 11 shows an enlarged view of an exemplary embodiment of the stent apparatus 150 of FIGS. 9 and 10. In this example, the wall 160 of the stent is made up of a series of undulating or zigzag wire support members 162 which are separated by interstices 164. The wire support members 162 may be arranged laterally or circumferentially around the cylindrical stent or they may be arranged longitudinally or diagonally with respect to the axis of the stent. The wire support members 162 may be formed from a single continuous piece of wire or they may be formed from a number of wire segments, which are then joined together. The undulating or zigzag wire support members 162 cross or overlap one another somewhat at a number of overlapping locations 168. In at least some of the overlapping locations 168 the wire support members 162 are not attached to one another, but are free to slide over one another. In alternate embodiments, the undulating wire support members 162 may be configured as mutually slidable, overlapping scales or other constructions to arrive at a similar geometry.

The wire support members 162 can be stimulated to move and/or change shape in response to a number of different stimuli. For example, the wire support members 162 can be excited by sonic or ultrasonic waves, which stimulates the wire support members 162 to vibrate which create a scrubbing action to remove deposits and/or new growth on the wire support members 162 and in the interstices 164 between them. Alternatively, the wire support members 162 can be stimulated to move by piezoelectric displacement or vibration transducers incorporated into the stent. The piezoelectric transducers can be activated by direct electrical connections to the stent or by inductive coupling to an implanted circuit by an extracorporeal or transesophageally placed voltage signal source.

As another alternative, some or all of the wire support members 162 may be fabricated of a thermally activated shape memory material, such as a nickel/titanium shape memory alloy or a thermally activated bimetallic strip, which changes its shape and/or dimensions in response to a change in temperature. Thus, the wire support members 162 can be actuated to perform a wiping action across the interstices 164 of the stent wall 160 by cycling the temperature of the implanted stent in situ. This wiping action of the wire support members 162 can also be actuated barometrically by incorporating pressure activated actuation members into the structure of the stent.

Figure 12:
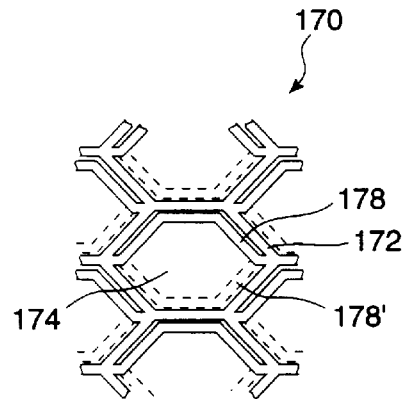
FIG. 12 is a magnified view of a second variation of the stent apparatus of FIG. 9.
Figure 13:
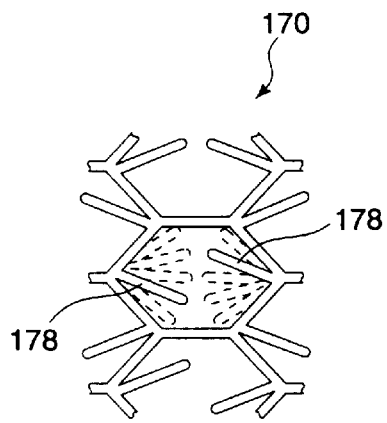
FIG. 13 is a magnified view of a third variation of the stent apparatus of FIG. 9.

FIGS. 12 and 13 show enlarged views of other exemplary embodiments of the stent apparatus 150 of FIGS. 9 and 10. In these examples, the wall 170 of the stent is formed by slotting and expanding a tubular member to form a pattern of support members 172 separated by openings or interstices 174. Within each opening 174 of the stent wall 170 is at least one wiper member 178. The wiper members 178 may be attached to the stent wall 170 at both ends, as in the example of FIG. 12. Alternatively, the wiper members 178 may be attached to the stent wall 170 at only one end and may operate singly or in pairs, as in the example of FIG. 13. The wiper members 178 can be controlled or actuated to move and/or change shape to create a wiping action across the openings 174 of the stent wall 170. In one preferred embodiment, the wiper members 178 are fabricated of a thermally activated shape memory material, such as a nickel/titanium shape memory alloy or a thermally activated bimetallic strip, which changes its shape and/or dimensions in response to a change in temperature. Thus, the wiper members 178 can be actuated to perform a wiping action across the interstices 174 of the stent wall 170 by cycling the temperature of the implanted stent in situ by any of the methods discussed above. This wiping action serves to remove any ingrowth of stenotic material intruding through the openings 174 of the stent wall 170.

Figure 14:
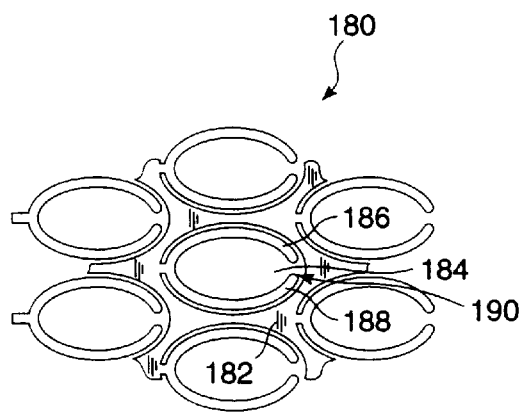
FIG. 14 is a magnified view of a fourth variation of the stent apparatus of FIG. 9.

FIG. 14 shows an enlarged view of another exemplary embodiment of the stent apparatus 150 of FIGS. 9 and 10. In this example, the wall 180 of the stent is made up of a series of support members 182 separated by openings or interstices 184. The support members 182 may be formed of wire or may be formed by slotting or cutting a tubular member to create a desired pattern of support members 182 and interstices 184. Within each opening 184 of the stent wall 180 is a tuning fork 190 with two arms 186, 188. The arms 186, 188 of the tuning fork 190 are manufactured to vibrate at a desired harmonic frequency which may be in the sonic or ultrasonic range. The tuning fork 190 can be stimulated to vibrate by applying sonic or ultrasonic waves to the implanted stent transcutaneously or intraluminally. Because there will be some variation of the harmonic frequency of the tuning forks 190 due to manufacturing variances and some damping of the harmonic frequency due to deposits or growth of tissue on the arms 186, 188 of the tuning forks 190, a frequency sweep should be applied to the stent to activate each of the tuning forks 190 to vibrate. Low amplitude vibrations of the tuning fork 190 will remove deposits and/or new growth of stenotic material on the arms 186, 188 of the tuning forks 190 and the support members 182 of the stent wall 180 to which they are connected. Higher amplitude vibrations of the tuning fork 190 will cause enough motion of the arms 186, 188 to create a wiping action to remove deposits and/or new growth of stenotic material intruding through the openings 184 of the stent wall 180 as well.

Alternatively, the tuning fork 190 can be stimulated to vibrate by piezoelectric vibration transducers incorporated into the stent. The piezoelectric vibration transducers can be activated by direct electrical connections to the stent or by inductive coupling to an external voltage signal source.

Figure 15:
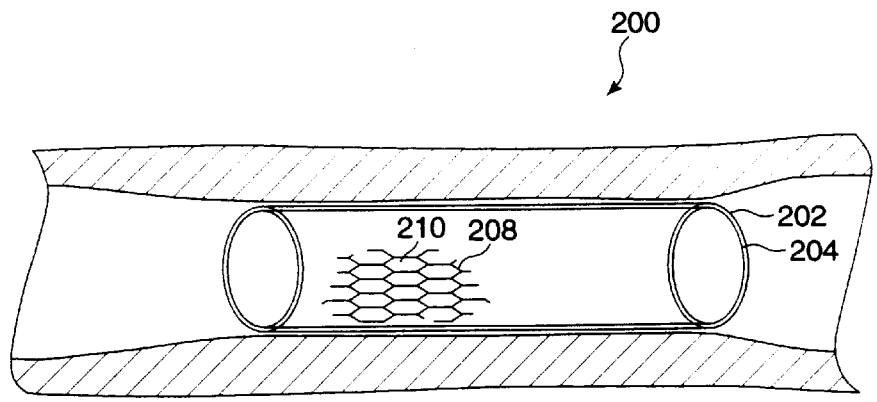
FIG. 15 shows a third embodiment of the stent apparatus of the present invention having an outer layer and a removable inner layer in the expanded or deployed state.

FIGS. 15–20 show another embodiment of the apparatus of the present invention. The apparatus comprises a stent 200 having an outer layer 202 and a removable inner layer 204, as shown in FIG. 15. The stent 200 is configured to have the general shape of a hollow, open-ended cylinder with an internal lumen 206. The stent 200 is deployable from a small diameter, compressed state to a larger diameter, expanded state. For use in coronary arteries or vein grafts, the stent 200 preferably has an expanded diameter from approximately 2 mm to 5 mm. For use in peripheral arteries, the stent 200 may have an expanded diameter from approximately 4 mm to 20 mm. For use in other body passages, the stent 200 should be adapted to have an expanded diameter approximately matching the desired luminal diameter of the body passage. The length of the stent 200 is highly variable. For use in coronary arteries, the stent 200 preferably has a length from approximately 20 to 60 mm. For use in peripheral arteries and other body passages, the stent 200 may be made considerably longer, if required. The stent 200 may be deployed by mechanical expansion means, such as by expanding an angioplasty balloon or other mechanical device within the lumen 206 of the stent 200. Alternatively, the stent 200 may be self-deploying, for example by elastic expansion or shape-memory expansion of the stent 200. Preferably, the outer layer 202 and the removable inner layer 204 of the stent 200 are deployed in the body passage simultaneously on a single delivery catheter. Alternatively, the outer layer 202 and the removable inner layer 204 may be deployed sequentially on the same or separate delivery catheters.

In a preferred embodiment, the outer layer 202 of the stent 200 comprises a matrix of support members 208 separated by openings or interstices 210. The support members 208 may be formed of wire or may be formed by slotting or cutting a tubular member to create a desired pattern of support members 208 and interstices 210. The removable inner layer 204 is coextensive with the outer layer 202 and is preferably made of a microporous or impermeable material which will serve as an effective barrier to ingrowth of stenotic material through the interstices 210 of the outer layer 202. The removable inner layer 204 may be bonded to the outer layer 202 with a non-permanent adhesive, particularly if the inner layer 204 is made of a flaccid material which will not be self supporting. To be effective as a barrier to ingrowth the inner layer 204 must be relatively impermeable. Additionally or alternatively, the inner layer 204 may contain an antimitotic agent to stop smooth cell proliferation. However, it may be detrimental to leave such an impermeable or bioactive liner in place long term. Therefore, it would be desire be able to remove the inner liner after the likelihood of restenosis has diminished.

Figure 16:
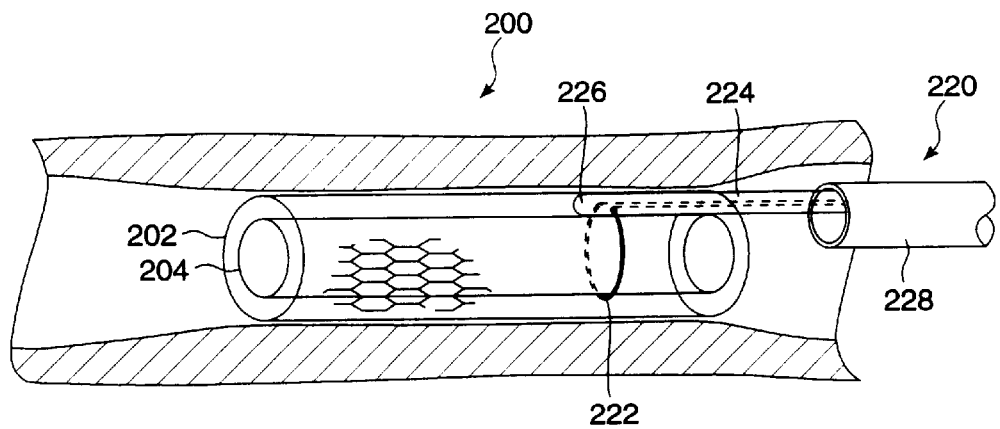
FIG. 16 shows the stent apparatus of FIG. 15 with a catheter for removing the inner layer of the stent.
Figure 17:
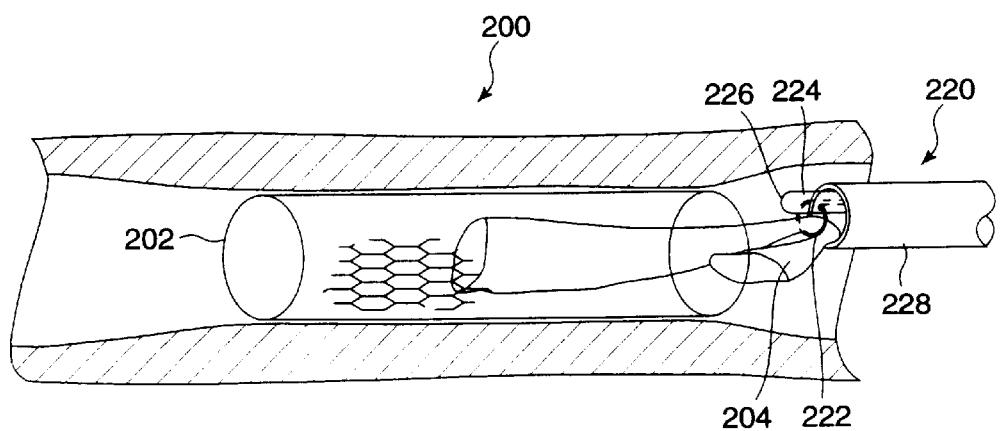
FIG. 17 shows the stent apparatus and catheter of FIG. 16 after removing the inner layer of the stent.

Consequently, in a preferred embodiment, the apparatus of the present invention will also comprise a means for removing and retrieving the removable inner layer 204 after implantation of the stent 200. The means for removing and retrieving the removable inner layer 204 may take one of several forms. In FIGS. 16 and 17 show a catheter 220 with a snare or grasper 222 for removing and retrieving the removable inner layer 204 of the stent 200. The catheter 220 has an elongated shaft 224 which is advanced through the vasculature to the site of the implanted stent 200. The distal end 226 of the shaft 224 is used to separate the removable inner layer 204 from the outer layer 202 of the stent 200, as shown in FIG. 16. The distal end 226 of the shaft 224 may be blunt or tapered or spatula shaped or a coaxial guidewire may be employed to aid in separating the inner layer 204 from the outer layer 202. Then, the snare or grasper 222 is used to capture the separated inner layer 204 and draw it into the outer tube 228 of the catheter 220, as shown in FIG. 17.

Figure 18:
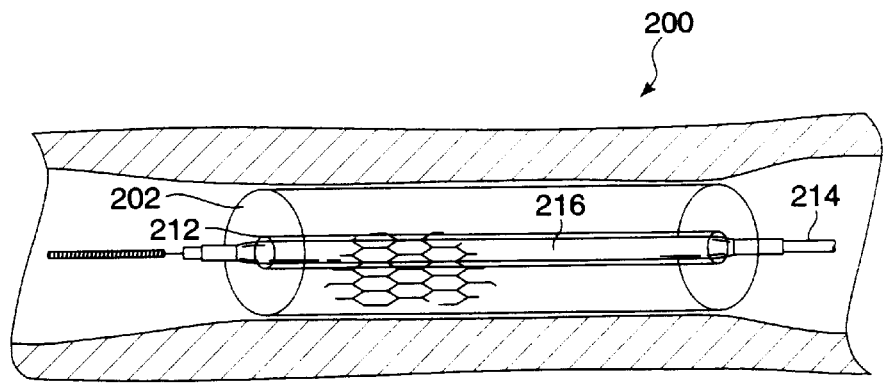
FIGS. 18, 19 and 20 are a series of drawings illustrating the optional method steps of replacing the removable inner layer of the stent apparatus of FIG. 15.
Figure 19:
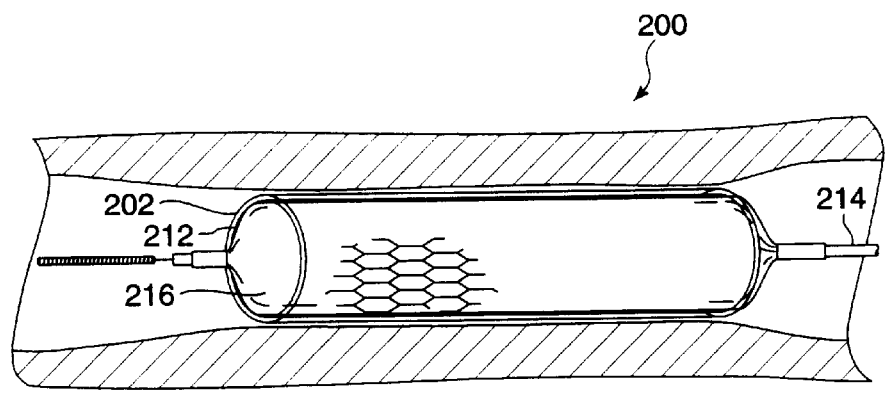
Figure 20:
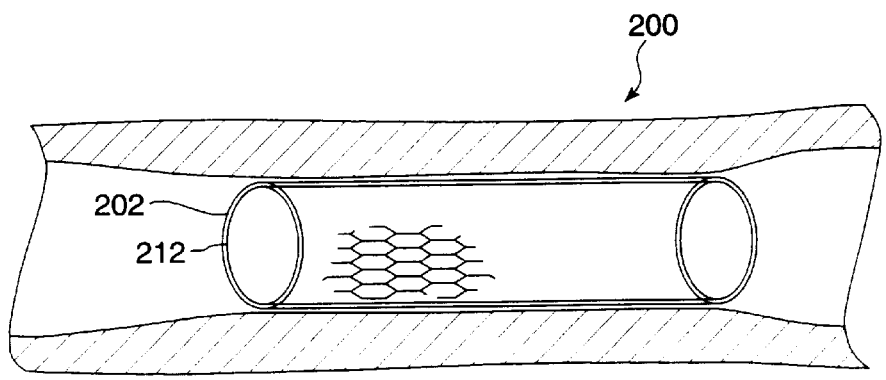

If it is felt that the likelihood of restenosis has not sufficiently diminished, a new inner layer 212 may be applied inside the outer layer 202 of the stent 200, according to the sequence of steps shown in FIGS. 18–20. To accomplish this, a dilatation catheter 214 having a new inner layer 212 mounted over the dilatation balloon 216 is advanced through the vasculature to the site of the implanted stent 200, as shown in FIG. 18. The dilatation balloon 216 is inflated to expand the new inner layer 212, as shown in FIG. 19. The new inner layer 212 will preferably have support members to hold it in place within the outer layer 202 once expanded. Alternatively, a non-permanent adhesive may be used to bond the new inner layer 212 in place, particularly if the new inner layer 212 is also made of a flaccid material which will not be self supporting. Afterward, the dilatation balloon 216 is deflated and the catheter 214 is withdrawn, leaving the new inner layer 212 in place, as shown in FIG. 20.

Figure 21:
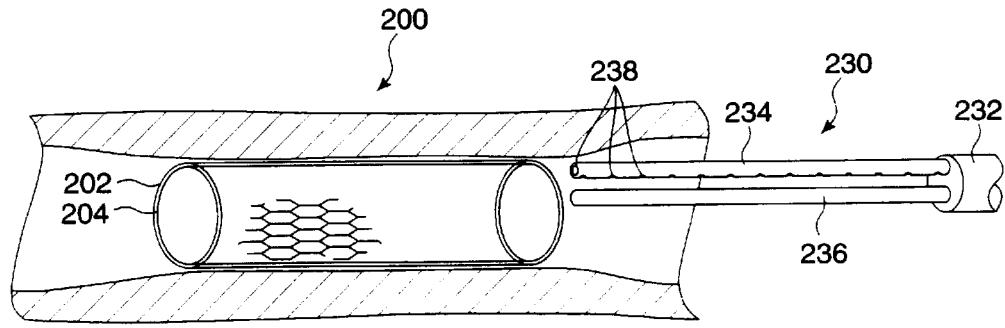
FIGS. 21, 22 and 23 show a variation of the stent apparatus of FIG. 15 with another variant of a catheter for removing the inner layer of the stent.
Figure 22:
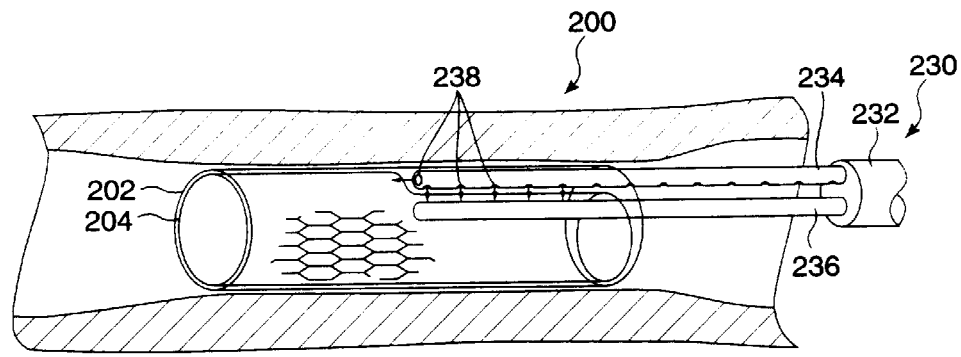
Figure 23:
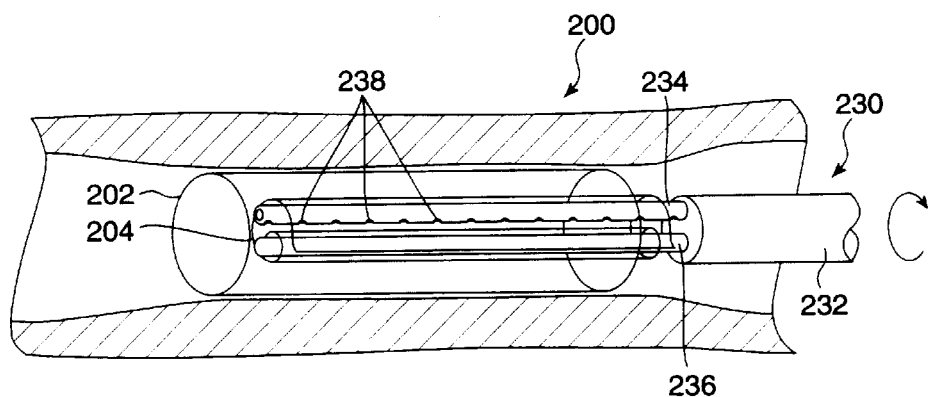

FIGS. 21–23 show another catheter 230 for removing and retrieving the removable inner layer 204 of the stent 200. The catheter 230 has an elongated shaft 232 that ends in two rods 234, 236. Preferably, at least one of the rods 234 has fluid flow orifices 238 in the distal end and/or the side of the rod 234. The catheter 230 is advanced through the vasculature to the site of the implanted stent 200, as shown in FIG. 21. One of the rods 234 is used to separate the removable inner layer 204 from the outer layer 202 of the stent 200. Fluid infused through the fluid flow orifices 238 may be used to help separate the removable inner layer 204 from the outer layer 202, as shown in FIG. 22. The catheter 230 is then rotated to wrap the removable inner layer 204 around the two rods 234, 236, as shown in FIG. 23. Vacuum aspiration through the fluid flow orifices 238 on one or both of the two rods 234, 236 may be used to help hold the removable inner layer 204 as it is withdrawn from the body passage.

Figure 24:
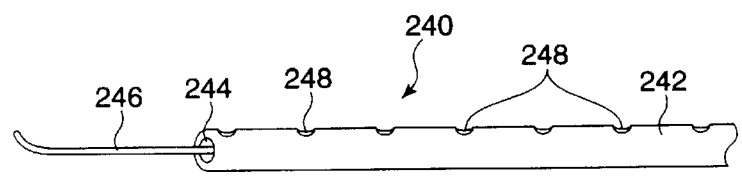
FIG. 24 shows another variant of a catheter for removing the inner layer of the stent apparatus of FIG. 15.
Figure 25:
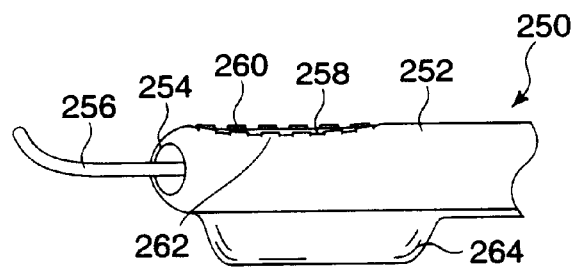
FIG. 25 shows another variant of a catheter for removing the inner layer of the stent apparatus of FIG. 15.
Figure 26:
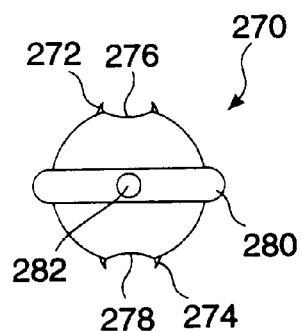
FIG. 26 shows another variant of a catheter for removing the inner layer of the stent apparatus of FIG. 15.

FIGS. 24–26 show three alternative catheters for removing and retrieving the removable inner layer 204 from the stent 200. FIG. 24 shows a side view of a vacuum grasper catheter 240 having an elongated catheter shaft 242 with a guidewire lumen 244 containing a coaxial guidewire 246 and one or more vacuum aspiration ports 248 for grasping the inner layer 204 of the stent 200 and removing it. The vacuum grasper catheter 240 can be used for removing the inner layer 204 of the stent 200 intact or aspirating it in pieces. FIG. 25 shows a side view of a vacuum scraper catheter 250 having an elongated catheter shaft 252 with a guidewire lumen 254 containing a coaxial guidewire 256. The distal portion of the catheter shaft 252 has an elongated vacuum aspiration port 258, which is flanked by a scraper or cutter 260. The scraper 260 may have a row of multiple scraping teeth 262. Opposite the vacuum aspiration port 258 and the scraper 260 is a biasing means 264, which may be an inflatable balloon similar to a dilatation balloon or a mechanical expander. The biasing means 264 is used to expand the catheter 250 within the stent 200 to press the scraper 260 against the inner surface of the stent 200. The catheter 260 is rotated to scrape the inner layer 204 and/or stenotic material from within the stent 200. Then, the inner layer 204 and/or the stenotic material removed is aspirated into the vacuum aspiration port 258. FIG. 26 shows an end view of a similar catheter 270 except that this catheter has two opposing cutters 272, 274 and two opposing vacuum aspiration ports 276, 278, with an expansion means 280, such as an inflatable balloon or a mechanical expander, between them. The catheter 270 may also include a guidewire lumen 282 for introducing the catheter 270 over a guidewire. The expansion means 280 is used to expand the catheter 270 within the stent 200 to press the cutters 272, 274 against the inner surface of the stent 200. The catheter 270 is rotated to scrape the inner layer 204 and/or stenotic material from within the stent 200. Then, the inner layer 204 and/or the stenotic material removed is aspirated into the vacuum aspiration ports 276, 278. Removal of the inner layer 204 of the stent 200 using any one of these catheters may be aided by cooling the inner layer 204 to a temperature below the glass transition temperature of the inner layer material to render it brittle and/or by applying ultrasonic energy to break up the inner layer 204.

Figure 27:
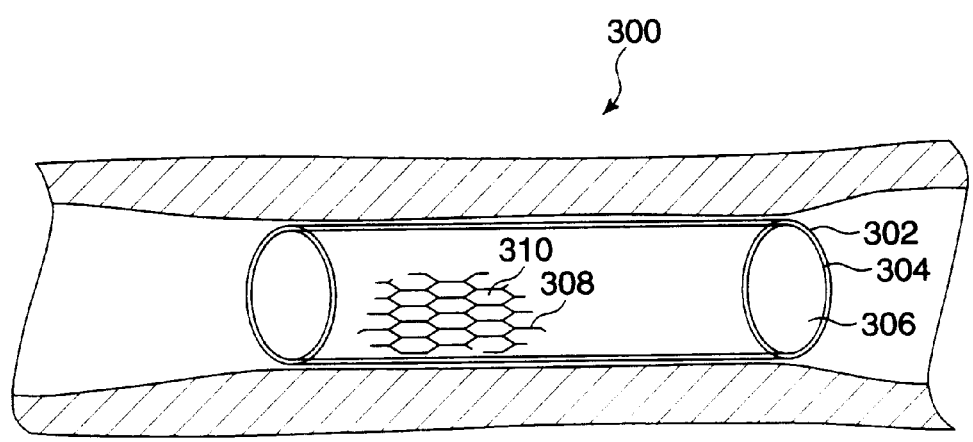
FIGS. 27, 28 and 29 show a variation of the stent apparatus of FIG. 15 with another variant of a catheter for removing the inner layer of the stent.
Figure 28:
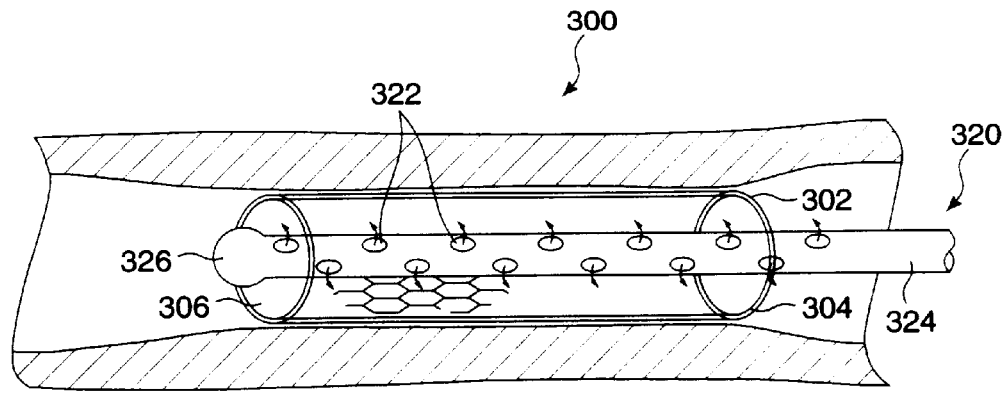
Figure 29:
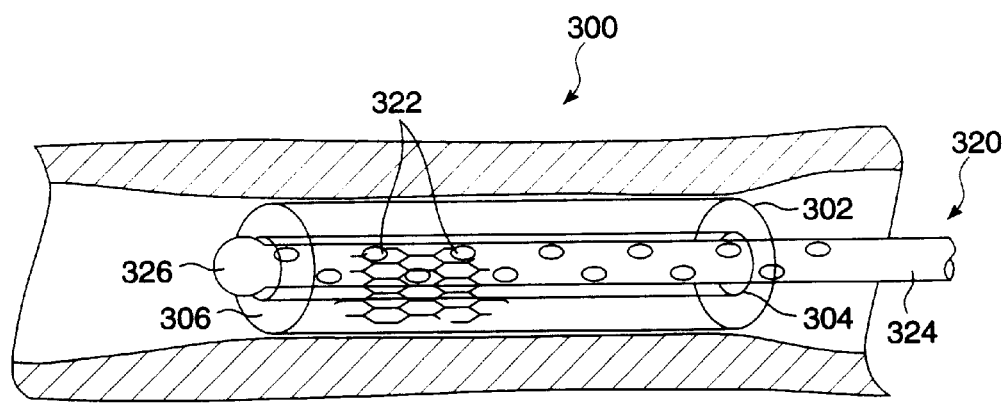

FIGS. 27–29 show another embodiment of the apparatus of the present invention comprising a stent 300 having an outer layer 302 and a removable inner layer 304, and a retrieval catheter 320 for removing and retrieving the removable inner layer 304 from the stent 300. The outer layer 302 of the stent 300 comprises a matrix of support members 308 separated by openings or interstices 310. The support members 308 may be formed of wire or may be formed by slotting or cutting a tubular member to create a desired pattern of support members 308 and interstices 310. The removable inner layer 304 is coextensive with the outer layer 302 and is preferably made of a metallic or polymeric material or a composite of materials having shape memory properties. The shape memory properties of the removable inner layer 304 may be triggered by a change in temperature or by exposure to a particular chemical solution. To remove the inner layer 304 from the implanted stent 300, the retrieval catheter 320 is advanced through the lumen 306 of the stent and a solution of hot or cold saline solution or a special chemical solution is infuse through the infusion ports 322 of the catheter 320. The infusate causes the removable inner layer 304 to shrink down around the shaft 324 of the catheter 320. Alternatively, the catheter 320 may include a heater, for example a resistive heater element or radiofrequency heating element, to heat the removable inner layer 304 and cause the removable inner layer 304 to shrink down around the shaft 324 of the catheter 320. A knob 326 or similar feature on the distal end of the catheter shaft 324, along with a vacuum drawn through the infusion ports 322, keeps the shrunken inner layer 304 on the catheter shaft 324 as the catheter 320 is withdrawn from the patient's body.

Figure 30:
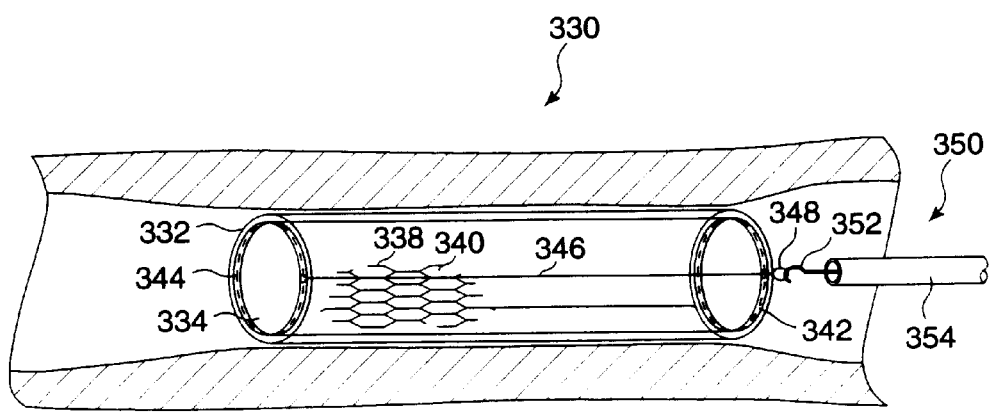
FIGS. 30 and 31 show a variation of the stent apparatus of FIG. 15 with another variant of a catheter for removing the inner layer of the stent.
Figure 31:
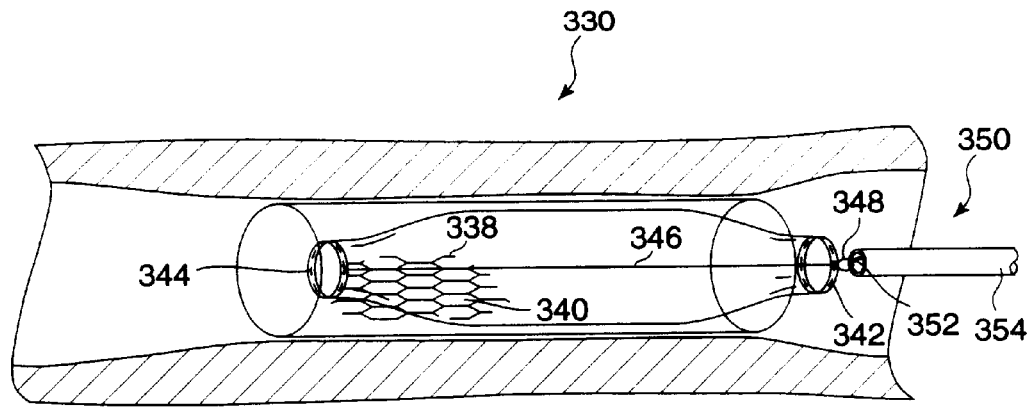

FIGS. 30 and 31 show another embodiment of the apparatus of the present invention comprising a stent 330 having an outer layer 332 and a removable inner layer 334, and a retrieval catheter 350 for removing and retrieving the removable inner layer 334 from the stent 330. The outer layer 332 of the stent 330 comprises a matrix of support members 338 separated by openings or interstices 340. The support members 338 may be formed of wire or may be formed by slotting or cutting a tubular member to create a desired pattern of support members 338 and interstices 340. The removable inner layer 334 is coextensive with the outer layer 332 and is preferably made of a flexible polymeric material or a flexible composite material. The removable inner layer 334 has incorporated into it a proximal purse string 342, a distal purse string 344, a pull cord 346 attached to both of the purse strings and a loop 348 at the end of the pull cord 346. The proximal purse string 342, the distal purse string 344 and the pull cord 346 may be made of wire or of suture material.

When it is desired to remove the inner layer 334 of the stent 330, the retrieval catheter 350 is advanced through the body passage to the site of the implanted stent 330. The loop 348 is grasped with an elongated hook member 352 that extends through the tubular body 354 of the catheter 350, as shown in FIG. 30. The hook member 352 is used to draw the loop 348 and the pull cord 346 into the tubular body 354 of the catheter 250. Pulling on the pull cord 346 causes the proximal purse string 342 and the distal purse string 344 to tighten, collapsing and closing off the ends of the removable inner layer 334 of the stent 330, as shown in FIG. 31. The catheter 350 and the collapsed inner layer 334 of the stent 330 are then withdrawn from the patient's body.

Figure 32:
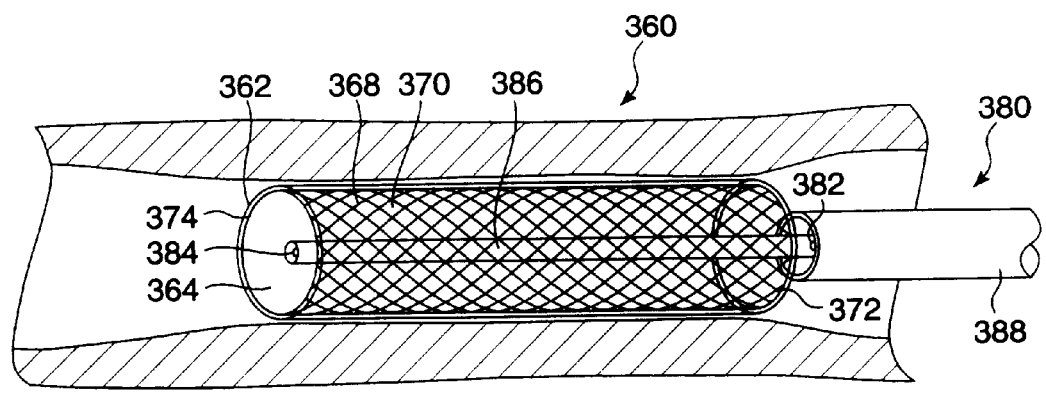
FIGS. 32 and 33 show a variation of the stent apparatus of FIG. 15 with another variant of a catheter for removing the inner layer of the stent.
Figure 33:
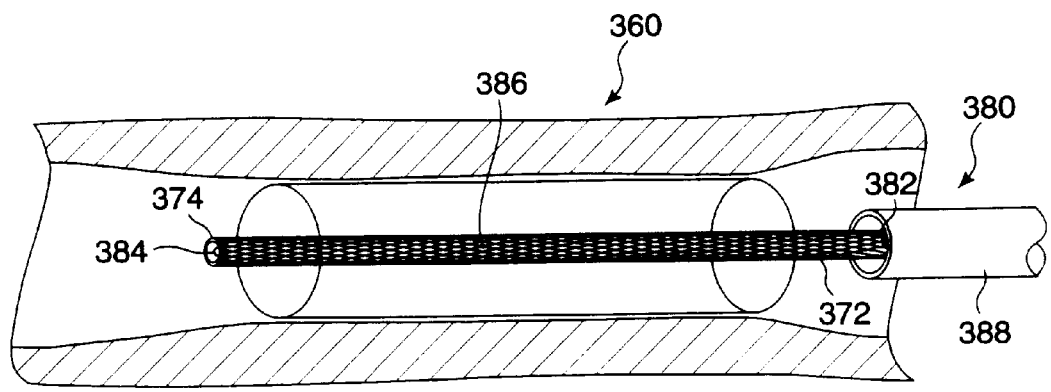

FIGS. 32 and 33 show another embodiment of the apparatus of the present invention comprising a stent 360 having an outer layer 362 and a removable inner layer 364, and a retrieval catheter 380 for removing and retrieving the removable inner layer 364 from the stent 360. The outer layer 362 of the stent 360 comprises a matrix of support members 368 separated by openings or interstices 370. The support members 368 may be formed of wire or may be formed by slotting or cutting a tubular member to create a desired pattern of support members 368 and interstices 370. The removable inner layer 364 is coextensive with the outer layer 362 and is preferably made of a metallic or polymeric mesh, a polymeric film or a composite material which shrinks diametrically when elongated longitudinally.

When it is desired to remove the inner layer 364 of the stent 360, the retrieval catheter 380 is advanced through the body passage to the site of the implanted stent 360. The proximal end 372 of the inner layer 364 is grasped with a first hook or grasper 382 on the shaft 388 of the catheter 380 and the distal end 374 of the inner layer 364 is grasped with a second hook or grasper 384 located at the distal end of an extension member 386 that is slidable within the tubular catheter shaft 388, as shown in FIG. 32. Then, the removable inner layer 364 is elongated by extending the extension member 386 distally from the catheter shaft 388, which collapses the inner layer 364 around the extension member 386, as shown in FIG. 33. The catheter 380 and the collapsed inner layer 364 of the stent 360 are then withdrawn from the patient's body.

FIGS. 34–37 show another embodiment of the apparatus of the present invention. The apparatus comprises a stent 400 which is specially adapted for facilitating removal of stenotic material from within the stent 400 and a catheter 420 which is adapted for use with the stent 400. The stent 400 is configured to have the general shape of a hollow, open-ended cylinder with an internal lumen 406. The stent 400 is deployable from a small diameter, compressed state to a larger diameter, expanded state. For use in coronary arteries or vein grafts, the stent 400 preferably has an expanded diameter from approximately 2 mm to 5 mm. For use in peripheral arteries, the stent 400 may have an expanded diameter from approximately 4 mm to 20 mm. For use in other body passages, the stent 400 should be adapted to have an expanded diameter approximately matching the desired luminal diameter of the body passage. The length of the stent 400 is highly variable. For use in coronary arteries, the stent 400 preferably has a length from approximately 20 mm to 60 mm. For use in peripheral arteries and other body passages, the stent 400 may be made considerably longer, if required. The stent 400 may be deployed by mechanical expansion means, such as by expanding an angioplasty balloon or other mechanical device within the lumen 406 of the stent 400. Alternatively, the stent 400 may be self-deploying, for example by elastic expansion or shape-memory expansion of the stent 400.

Figure 34:
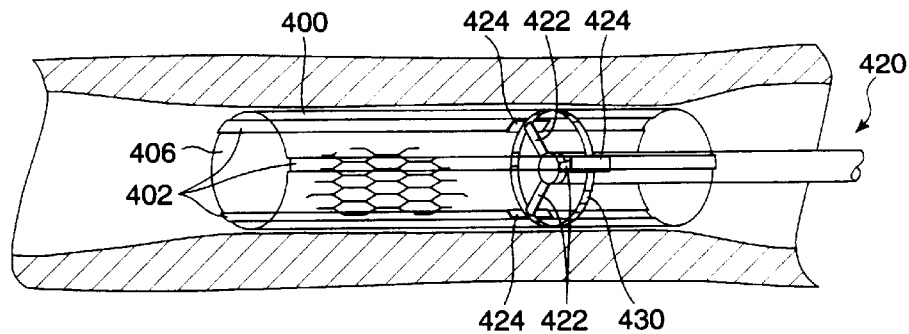
FIGS. 34 and 35 show a side perspective view and an end view, respectively, of a fourth embodiment of the stent apparatus of the present invention and a catheter apparatus for removing stenotic material from the stent.
Figure 35:
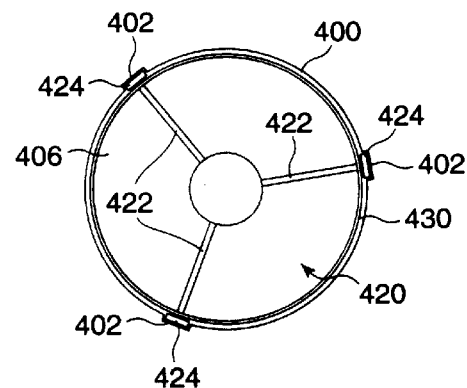

The stent 400 is made with at least one internal rail 402, which may be a slot that goes all the way through the wall 404 of the stent 400 or a groove 402 that goes only part way through the wall 404 of the stent 400. The at least one rail 402 may be arranged longitudinally, circumferentially or diagonally with respect to the stent 400. By way of example, FIG. 34 shows a stent 400 with three rails 402 arranged longitudinally with respect to the stent 400. The catheter 420 is made with a like number of legs 422 that end in feet 424, which are specially shaped to ride in the slots or grooves of the rails 402. This is best seen in the end view of FIG. 35. The feet 424 guide the catheter 420 longitudinally along the rails 402 on the interior of the stent 400. Preferably, the legs 422 are extendable and retractable from the tubular shaft 426 of the catheter 420. When extended, the legs 422 keep the tubular shaft 426 of the catheter 420 centered within the stent 400. A stenotic material removal mechanism, which is indicated generically by lines 430, is attached to the catheter 420. The stenotic material removal mechanism 430 can be a cutter, a brush, an abrasion tool, an ablation device, a vacuum aspiration device or any other means for removing stenotic material from within the stent 400. Various means for removing stenotic material from within a stent are described in commonly owned, copending patent applications Ser. Nos. 08/798,722 and 08/857,659, which are hereby incorporated by reference in their entirety. The internal rails 402 of the stent 400 guide the stenotic material removal mechanism 430 and keep it centered within the stent 400 for effective removal of stenotic material without damage to the stent 400 or to the native vessel walls surrounding the stent 400.

Figure 36:
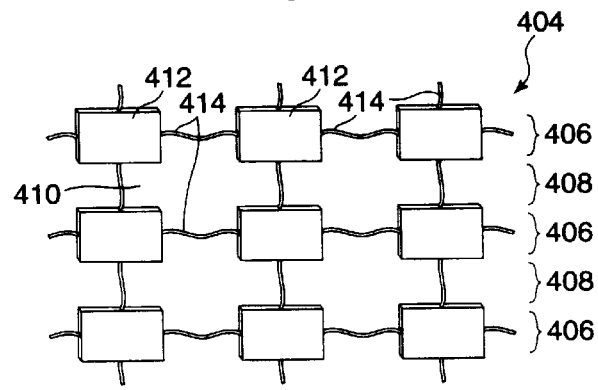
FIGS. 36 and 37 are a magnified side view and an end view, respectively, of a variation of the stent apparatus of FIGS. 34 and 35.
Figure 37:
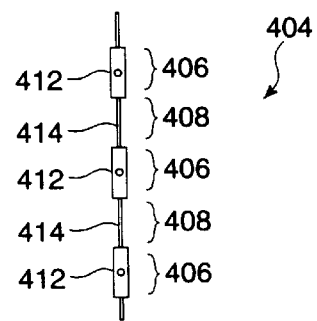

FIGS. 36 and 37 show a magnified view of an embodiment of an expandable stent 404 having alternating raised rails 406 and grooves 408. The stent wall 404 is made up of a multiplicity of bosses 412 which are interconnected by a network of expandable members 414. When the stent 404 is deployed, the expandable members 414 elongate, expanding the openings or interstices 410 within the wall 404 and allowing the stent 400 to expand in diameter. The bosses 412 are raised above the expandable members 414, creating a pattern of alternating raised rails 406 and grooves 408 longitudinally and circumferentially around the stent 404, as seen in end view in FIG. 37. The feet 424 of the catheter 420 can be adapted to ride along the raised rails 406 or the grooves 408 longitudinally and/or circumferentially around the stent 404.

Figure 38:
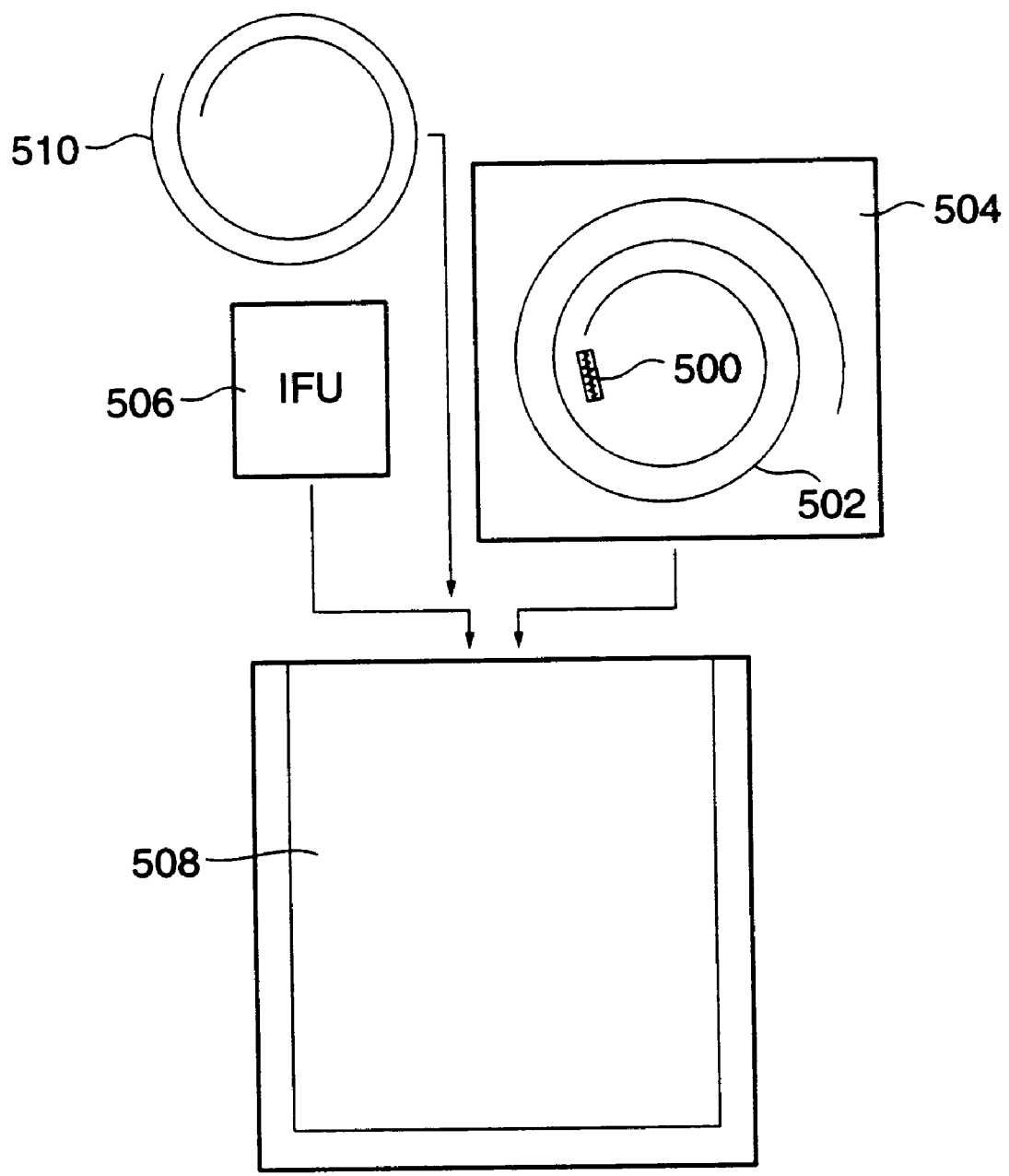
FIG. 38 illustrates a kit including a stent, a catheter, a package and instructions for use according to the present invention.

Referring now to FIG. 38, a catheter kit according to the present invention comprises a stent 500 and a stent delivery catheter 502, commonly mounted on a board or in a tray 504, instructions for use (IFU) 506, and a pouch 508 or other conventional package. A retrieval catheter or a stenotic material removal catheter 510 may be packaged together with the catheter kit or separately. The instructions for use (IFU) 506 are typically part of a separate sheet or booklet which, together with the stent 500 and a stent delivery catheter 502, is packaged within the pouch 508 or other packaging material. The packaging and its contents will preferably be sterile or sterilizable. The instructions for use (IFU) 506 will set forth method steps comprising the method(s) as described above.

Although the method of the present invention has been described using the example of revascularizing restenosed coronary arteries, it should be noted that the methods and apparatus disclosed may be used for reopening any previously stented body passage which has been subject to restenosis or reclosure. Other body passages where these methods and apparatus may apply include the peripheral blood vessels, the urinary tract, the digestive tract and the respiratory tract.

What is claimed is:

1. Apparatus for maintaining an open lumen in a body passage, comprising:

a stent having support members defining a generally cylindrical envelope for supporting a wall of the body passage and openings between the support members of the stent, the stent having at least one internal rail on an inner surface of the stent; and a catheter device for removing stenotic material from within the stent, the catheter device having at least one guide means for continuous guiding the catheter device along a linear path of sand at least one internal rail on the inner surface of the stent.

2. The apparatus of claim 1 wherein the at least one internal rail comprises a slot or groove on the inner surface of the stent and the guide means comprises a guide foot for slidably engaging the slot or groove.

3. The apparatus of claim 1 wherein the stent comprises three longitudinally oriented internal rails on the inner surface of the stent and the catheter device has three guide means for guiding the catheter device along the three internal rails.

4. The apparatus of claim 3 wherein the three longitudinally oriented internal rails comprise three slots or grooves on the inner surface of the stent and the three guide means comprise three guide feet for slidably engaging the slots or grooves.

\* \* \* \* \*